US008221358B2

(12) United States Patent
McKay

(10) Patent No.: US 8,221,358 B2
(45) Date of Patent: Jul. 17, 2012

(54) DEVICES AND METHODS FOR DELIVERING DRUG DEPOTS TO A SITE BENEATH THE SKIN

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 168 days.

(21) Appl. No.: 11/942,820

(22) Filed: Nov. 20, 2007

(65) Prior Publication Data
US 2009/0131908 A1 May 21, 2009

(51) Int. Cl.
A61M 5/00 (2006.01)
(52) U.S. Cl. .......................... 604/187; 604/511
(58) Field of Classification Search .................. 604/187, 604/188, 164.12, 60, 158
See application file for complete search history.

(56) References Cited

U.S. PATENT DOCUMENTS

| | | | |
|---|---|---|---|
| 1,881,854 A | 10/1932 | Muir | |
| 4,105,030 A | 8/1978 | Kercso | |
| 4,427,015 A * | 1/1984 | Redeaux, Jr. | 600/578 |
| 4,451,253 A * | 5/1984 | Harman | 604/60 |
| 4,909,250 A | 3/1990 | Smith | |
| 5,024,655 A | 6/1991 | Freeman et al. | |
| 5,207,678 A | 5/1993 | Harms et al. | |
| 5,212,162 A | 5/1993 | Missel et al. | |
| 5,928,130 A | 7/1999 | Schmidt | |
| 6,193,692 B1 * | 2/2001 | Harris et al. | 604/164.02 |
| 6,450,937 B1 * | 9/2002 | Mercereau et al. | 600/7 |
| 6,471,688 B1 | 10/2002 | Harper et al. | |
| 6,565,541 B2 * | 5/2003 | Sharp | 604/192 |
| 7,001,892 B1 | 2/2006 | Chmielewski et al. | |
| 7,081,123 B2 * | 7/2006 | Merboth et al. | 606/185 |
| 7,252,651 B2 | 8/2007 | Haider et al. | |
| 2001/0043915 A1 | 11/2001 | Frey, II | |
| 2003/0036673 A1 | 2/2003 | Schmidt | |
| 2003/0171637 A1 * | 9/2003 | Terwilliger et al. | 600/1 |
| 2003/0233101 A1 | 12/2003 | Lubock et al. | |
| 2004/0015133 A1 | 1/2004 | Karim | |
| 2004/0111118 A1 | 6/2004 | Hill et al. | |
| 2004/0220546 A1 | 11/2004 | Heruth et al. | |
| 2004/0220547 A1 | 11/2004 | Heruth et al. | |
| 2004/0220548 A1 | 11/2004 | Heruth et al. | |
| 2005/0070843 A1 | 3/2005 | Gonzales | |
| 2005/0137579 A1 | 6/2005 | Heruth et al. | |
| 2006/0046961 A1 | 3/2006 | McKay et al. | |
| 2006/0253100 A1 | 11/2006 | Burright et al. | |
| 2006/0264839 A1 | 11/2006 | Veasey et al. | |
| 2007/0055378 A1 | 3/2007 | Ankney et al. | |
| 2007/0219564 A1 | 9/2007 | Rue et al. | |

FOREIGN PATENT DOCUMENTS

| | | |
|---|---|---|
| EP | 1216721 A2 | 6/2002 |
| EP | 1518549 B1 | 2/2007 |
| FR | 1270590 A | 9/1961 |
| FR | 2007684 A | 1/1970 |
| FR | 2231355 A | 12/1974 |
| GB | 1379358 | 1/1975 |

OTHER PUBLICATIONS

Lupron Depot Package Insert.
Norplant Package Insert.

* cited by examiner

Primary Examiner — Kevin C Sirmons
Assistant Examiner — Brandy C Scott

(57) ABSTRACT

Devices and methods are provided for delivering a drug depot at or near the spinal column of a patient. In various embodiments, the drug depot comprises a drug cartridge containing drug pellets for delivery at or near the spinal column of a patient.

19 Claims, 4 Drawing Sheets

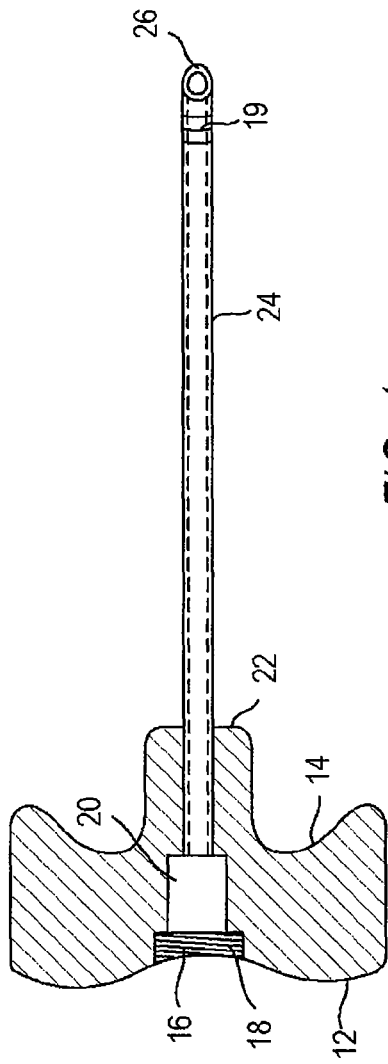
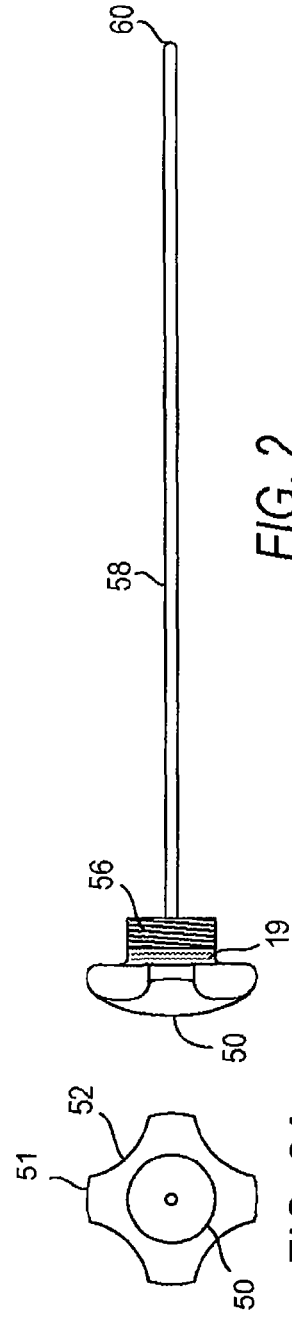
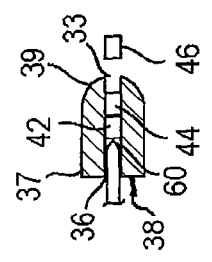
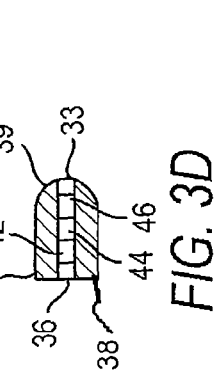
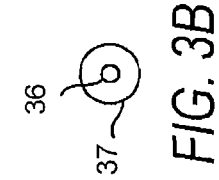
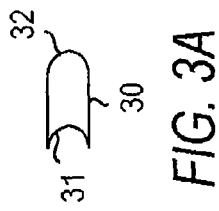

DEVICES AND METHODS FOR DELIVERING DRUG DEPOTS TO A SITE BENEATH THE SKIN

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient (e.g., subcutaneously or intramuscularly) so that the drug is slowly released over a long period of time. Such drug depots allow the drug to be released from the depot in a relatively uniform dose over a time period. This method of administering drugs is becoming especially important and popular in modulating hormonal replacement or contraception.

Previously, drug depots and other types of implants have been inserted into the treatment site beneath the skin by use of a large bore trocar device, which is a two-piece device that includes a cannula and an obdurator. The large size of the trocar device requires an incision to be made through the skin at the site of implant of the drug depot using a separate instrument (e.g., scalpel). A cannula and obdurator are inserted together through the skin at the incision site. Next, the obdurator is withdrawn, leaving the cannula in place as a guide for inserting the drug depot. The drug depot is inserted through the cannula, and the obdurator is used to push the implant to the end of the cannula. The cannula and obdurator are then withdrawn completely, leaving the implant in place beneath the skin.

Typically, because of the large size of the trocar devices, their use is limited to subcutaneously delivery of the drug depot over a large area (e.g., 2-2.5 inches), with a typical drug depot in the order of 1½ inches long. Thus, the trocar device is not suitable for many treatment sites because it lacks precision and may cause additional trauma to the tissue surrounding the desired site of implant.

Other drug depot devices have been developed to simplify implanting the drug depots. These devices have a handle for one-handed implantation of the drug depot, a small needle containing the drug depot to be implanted and a rod positioned within the needle for pushing the drug depot out of the needle. Once the needle containing the drug depot has been inserted at the site of implant, a spring loaded trigger on the handle is activated which causes the needle to be automatically withdrawn by a spring leaving the implanted drug depot in place. Unfortunately, it is not possible to control the motion of the needle in these devices because the needle will automatically retract upon activation of the trigger. The complex spring loaded propelling system and trigger of these devices increase the chances that the device will jam and fail to eject the drug depot when required.

Conventional needle and syringe devices have been used to implant a drug solution or suspension to sites such as, for example, the epidural space. These devices typically utilize a syringe preloaded with the drug solution and an epidural needle. The needle is inserted through the skin, supraspinus ligament, intraspinus ligament, ligamentum flavum and then into the epidural space. The drug solution is delivered through the needle to the epidural space using the syringe plunger. Conventional needle and syringe devices often do not easily allow controlled and precision implant of the drug depot. If multiple drug depot implants are needed, these conventional needle and syringe devices often do not allow accurate placement of the implant in a manner to optimize location, accurate spacing, and drug distribution.

New drug depot devices are needed, which can easily allow accurate and precise implantation of a drug depot with minimal physical and psychological trauma to a patient. When implanting several drug depots, a drug depot device is needed that accurately and precisely allows placement of the drug depot in a manner to optimize location, accurate spacing, and drug distribution.

SUMMARY

New drug depot devices, which can easily allow accurate and precise implantation of a drug depot with minimal physical and psychological trauma to a patient are provided. One advantage of the drug depot device is that it allows the user to "dial a dose" or "push a dose" of the drug depot to implant it. Another advantage of the drug depot device is, in various embodiments, when several drug depots are to be implanted, the drug depot device allows accurate placement of the drug depot in a manner to optimize location, accurate spacing, and drug distribution. The drug depot device, in various embodiments, includes a drug cartridge containing one or more drug pellets that has the advantages of easily being sterilized, loaded into a drug depot chamber and released from the device to a site beneath the skin of a patient (e.g., at or near the spinal column).

In one exemplary embodiment, a device is provided for delivering a drug depot to a site at or near the spinal column of a patient, the device comprising: a cannula having a proximal end and a distal end, the proximal end of the cannula having an opening to receive the drug depot, the distal end of the cannula capable of insertion at or near the spinal column and having an opening for passage of the drug depot; and a plunger being slidably receivable within the opening of the proximal end of the cannula, the plunger having a first end and a tip at a second end, the first end being capable of moving the tip of the plunger to an extended position, wherein the openings of the proximal and distal ends permit passage of the drug depot and wherein the movement of the tip of the plunger to the extended position causes delivery of the drug depot from the distal end of the cannula to the site at or near the spinal column of the patient.

In another exemplary embodiment, a device is provided for delivering a drug depot to a site beneath the skin of a patient, the device comprising: a needle having a proximal end and a distal end, the proximal end of the needle having an opening to receive the drug depot and a generally cylindrical hub surrounding the opening of the proximal end of the needle, the distal end of the needle having a tip capable of passage through the skin of the patient and an opening for passage of the drug depot; and a plunger being slidably receivable within the opening of the proximal end of the needle and movable to an extended position, the plunger having a knob at a first end and a tip at a second end, the knob having threading for engaging the hub of the needle and the hub of the needle comprising threading for engaging the knob of the plunger, wherein rotation of the knob of the plunger along the threading of the hub moves the tip of the plunger to the extended position so as to effect delivery of the drug depot from the distal end of the needle to beneath the skin of the patient.

In yet another exemplary embodiment, a device is provided for delivering a drug depot to a site at or near the spinal column of a patient, the device comprising: a cannula having a proximal end and a distal end, the distal end of the cannula capable of insertion to the site beneath the skin of the patient and having an opening for passage of the drug depot, the proximal end of the cannula attached to a depot chamber, the drug depot chamber having an opening to receive the drug depot; and a plunger being slidably receivable within the opening of the drug depot chamber and within the cannula, the plunger having a first end and a tip at a second end, the first end for moving the tip of the plunger to an extended position, wherein the openings of the depot chamber and distal end permit passage of the drug depot and wherein the movement of the tip of the plunger to the extended position causes delivery of the drug depot from the distal end of the cannula to the site at or near the spinal column of the patient.

In still yet another exemplary embodiment, a drug cartridge is provided for delivering a drug pellet to a site beneath the skin of a patient, the drug cartridge comprising: one or more drug pellets contained within a channel of the drug cartridge, the drug cartridge having a proximal end and a distal end, the proximal end of the drug cartridge having an opening to receive the one or more drug pellets and a plunger, the distal end of the cartridge having an opening for receiving the plunger and passage of the drug depot, wherein movement of the plunger to an extended position moves the one or more drug pellets within the channel of the cartridge out the distal end of the drug cartridge.

In still yet another exemplary embodiment, a method is provided for delivering a drug depot to a site beneath the skin of a patient, the method comprising: providing a device for delivering a drug depot, the device comprising a cannula having a proximal end and a distal end, the proximal end of the cannula having an opening to receive the drug depot, the distal end of the cannula capable of insertion to the site beneath the skin of the patient and having an opening for passage of the drug depot; and a plunger being slidably receivable within the opening of the proximal end of the cannula, the plunger having a first end and a tip at a second end, the first end being capable of moving the tip of the plunger to an extended position; inserting the distal end of the cannula and/or plunger to the site beneath the skin of the patient; loading the drug depot for delivery in the cannula; and positioning the plunger within the cannula and moving the plunger in the extended position thereby delivering the drug depot from the distal end of the cannula to the site beneath the skin of the patient.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 1 illustrates a side sectional view of an embodiment of the cannula or needle of the drug depot device. In this illustrated embodiment, the cannula or needle includes a pellet chamber having a generally cylindrical hub surrounding the pellet chamber and a handle disposed around the hub, pellet chamber, cannula or needle for ease of insertion.

FIG. 2 illustrates a side sectional view of an embodiment of the plunger having a knob and engagement means for engaging the plunger. FIG. 2A illustrates a radial view of an embodiment of the plunger that has recesses for the user to rotate the knob of the plunger.

FIG. 2B illustrates an expanded view of an embodiment of the plunger tip, which may be complementary to the proximal end of the pellet that allows easier drug delivery.

FIG. 3A illustrates a side view of an embodiment of a drug depot in the form of a drug pellet shown in a bullet shape. FIG. 3B illustrates a radial view of an embodiment of a drug depot in the form of a drug cartridge that has a proximal opening for loading the drug pellet and for receiving the plunger tip. FIG. 3C illustrates a side sectional view of an embodiment of a single dose drug cartridge that has a channel, which contains one pellet in the channel. FIG. 3D illustrates a side view of an embodiment of a multi-dose drug cartridge that has a channel, which contains three pellets. FIG. 3E illustrates a side view of a cartridge that has a channel that can guide the plunger tip and allows release of a pellet.

Figure 4:
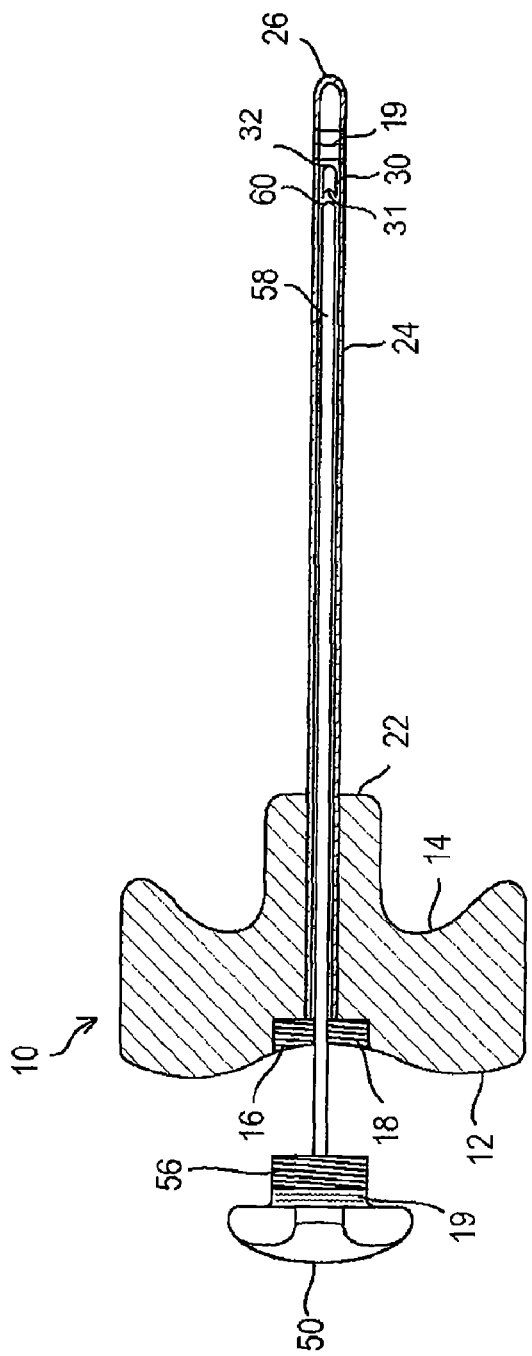
FIG. 4 illustrates a side view of an embodiment of the drug depot device loaded with a drug pellet. The plunger is in one of the retracted positions.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug depot devices, which can easily allow accurate and precision implant of a drug depot with minimal physical and psychological trauma to a patient are provided. In various embodiments the drug depot device allows the user to dial a dose of the drug depot to implant by precisely controlling implant location, accurate spacing, and drug distribution. In various embodiments, when several drug depots are to be implanted, a drug depot device is provided that accurately allows placement of the drug depot in a manner to optimize location, accurate spacing, and drug distribution. In various embodiments, the drug depot device includes a drug cartridge containing one or more drug pellets that can easily be sterilized and loaded into the drug depot device.

In one exemplary embodiment, a device is provided for delivering a drug depot to a site beneath the skin of a patient (e.g., at or near the spinal column), the device comprising: a cannula having a proximal end and a distal end, the proximal end of the cannula having an opening to receive the drug depot, the distal end of the cannula capable of insertion to the site beneath the skin of the patient and having an opening for passage of the drug depot; and a plunger being slidably receivable within the opening of the proximal end of the cannula, the plunger having a knob at a first end and a tip at a second end, the knob comprising engagement means for engaging the proximal end of the cannula and being capable of movement that in turn moves the tip of the plunger to an extended position, wherein the openings of the proximal and distal ends permit passage of the drug depot and wherein the movement of the tip of the plunger to the extended position causes delivery of the drug depot from the distal end of the cannula to the site beneath the skin of the patient.

Cannula or Needle

The drug depot device comprises a cannula or needle having a proximal end and a distal end, the proximal end of the cannula having an opening to receive the drug depot, the distal end of the cannula capable of insertion to the site beneath the skin of the patient and having an opening for passage of the drug. FIG. 1 illustrates a side view of an embodiment of the needle or cannula of the drug depot device. In this illustrated embodiment, the needle or cannula 24 has a proximal end in the direction of the opening 16, which receives the drug depot. The distal end of the cannula or needle is capable of insertion to the site beneath the skin of the patient (e.g., at or near a spinal column site) and has an opening 26 for passage of the drug depot. In the embodiment shown in FIG. 1, the drug depot device has a drug depot chamber 20 attached to the cannula or needle and has an opening 16 for loading the drug depot for delivery.

The cannula or needle of the drug depot device is designed to cause minimal physical and psychological trauma to the patient. The term "patient" can refer to animals, including, without limitation, humans.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The cannula or needle of the drug depot device has a diameter that is larger than the diameter of at least part of the plunger (e.g., tip, middle, etc.) to allow at least part of the plunger to be slidably received within the cannula or needle. In various embodiments, the diameter of the cannula or needle is substantially the same throughout. In other embodiments, the diameter of the needle or cannula becomes smaller approaching the distal end for drug delivery. For example, in various embodiments when the device does not have a drug depot chamber, the drug depot may be loaded within the proximal end of the cannula or needle and the plunger will, in the extended position, slide the drug depot and dispense the drug depot from the distal end (shown in FIG. 5). In various embodiments, when the drug depot comprises a drug cartridge containing drug pellets, and when the plunger is moved to the extended position, the drug cartridge will remain within the cannula or needle and the channel of the drug cartridge will guide the tip of the plunger longitudinally and the drug pellet will be released in the extended position (shown in FIG. 5).

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the needle, cannula or plunger may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina and implanting the drug depot.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, the handle, first end, knob, plunger or hub includes dose indicator markings (e.g., numbers, lines, letters, radiographic markers, etc.) to indicate the number of drug depots delivered in this way the user can "dial a dose" for the drug depot to be delivered. In various embodiments, the plunger, cannula or drug depot include markings that indicate location at or near the site beneath the skin. FIG. 1 illustrates markings 19 on the distal end of the cannula. These markings, in various embodiments, allow the user to indicate location at or near the site beneath the skin.

Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot chamber 20 is capable of receiving one or more drug depots and the tip of the plunger. Typically, the drug depot chamber is the same size or larger than the diameter of the cannula or needle and larger than the diameter of the drug depot and cartridge. The drug depot chamber may be made of the same or different materials as the cannula or needle. Such materials include, but are not limited to polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

In alternative embodiments (not shown), the drug depot chamber may have its own opening for loading the drug depot directly into the drug depot chamber and the proximal end of the cannula or needle has its own proximal end opening which is axially aligned with the drug depot chamber opening. The cannula or needle opening and the drug depot opening allow a plunger to be slidably received within.

Figure 5:
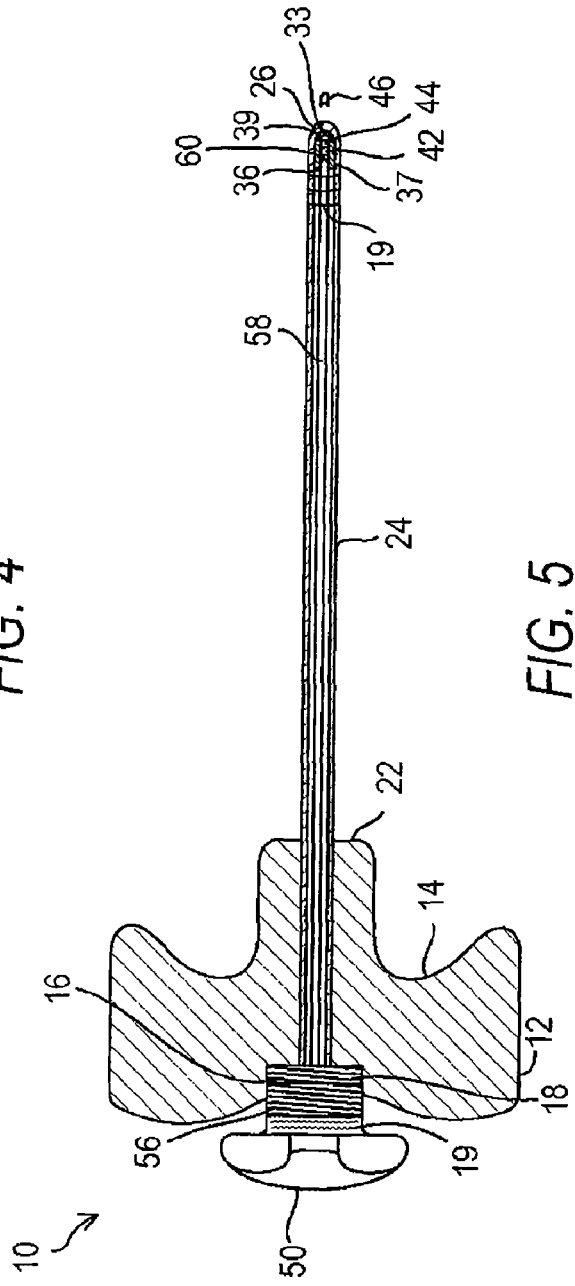
FIG. 5 illustrates a side view of an embodiment of the drug depot device loaded with a drug cartridge. The plunger is in an extended position and the drug cartridge is retained in the device, while the drug pellet is delivered out the distal end of the cannula or needle.

In various embodiments, the drug depot comprises a drug cartridge containing drug pellets loaded within the drug depot chamber, when the plunger may be moved to the extended position, the drug cartridge will remain within the cannula or needle and the channel of the drug cartridge will guide the tip of the plunger longitudinally and the drug pellet will be released in the extended position (shown in FIG. 5).

In various embodiments, surrounding the opening 16 of the proximal end of the cannula or needle is a generally cylindrical hub 18 having an engagement means (shown as internal threading) for engaging the knob of the plunger. Engagement means include, but are not limited to, threading, tracks, clips, ribs, projections, indentations, friction, or the like that allow the plunger knob to be turned or pushed, which in turn moves the plunger toward or out the distal end of the cannula or needle. The engagement means may be disposed on the generally cylindrical hub, on the plunger or on the handle. The engagement means, in various embodiments, may lock the plunger and prevent unintended insertion of the drug depot.

The drug depot device, in various embodiments, comprises a handle 12 disposed around the hub, cannula, and or drug depot chamber. The handle may have contours 14 and for easily grasping the device during use for insertion of the drug depot. The handle can be angled for right and left hand users or can be generic for both hands.

Plunger

FIG. 2 illustrates a side sectional view of an embodiment of the plunger 58. The plunger may be made of the same materials as the cannula or needle. The plunger 58 may have a knob 50 and engagement means 56 (shown as external threading) for engaging the internal threading of the handle or hub (18 of FIG. 1). Although the first end of the plunger is shown as a knob 50, it will be understood that the knob can be a top, dial, cap, handle or any member that allows the user to utilize the plunger. The plunger has a second end that includes a tip 60, which is capable of moving the drug depot within the cannula. In other embodiments, the tip of the plunger is sufficiently pointed so that it is capable of insertion to the site beneath the skin of the patient and the cannula or needle is blunted and used to guide the drug depot to the site. In various embodiments, the first end of the plunger allows the user to move plunger toward the distal end of the cannula or needle longitudinally along the axis of the cannula or needle to deliver the drug depot (e.g., by pushing the first end of the plunger toward the distal end of the cannula or needle).

In various embodiments, the plunger engages the cannula or needle and the friction from the plunger engaging the cannula allows controlled movement of the plunger within the cannula or needle to deliver the drug depot to the site. In this way, the device, in various embodiments, allows precisely controlling implant location, accurate spacing, and drug distribution.

The plunger has a diameter less than the cannula or needle so that it can be slidably received therein. The plunger may be longer, shorter, the same size, or smaller in length than the cannula or needle. In embodiments where the plunger extends from the distal end of the cannula or needle, the plunger is usually longer than the cannula or needle.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The plunger may optionally include one or more tapered regions.

Like the cannula or needle, in various embodiments, the plunger may have dose indicator markings (e.g., numbers, lines, letters, radiographic markers, etc.) to indicate the number of drug depots delivered. In this way, the user can "dial a dose" for the drug depot to be delivered. In various embodiments, the plunger includes markings that indicate location at or near the site beneath the skin. FIG. 2 illustrates markings 19 on the knob of the plunger. These markings, in various embodiments, allow the user to indicate location at or near the site beneath the skin.

FIG. 2A illustrates a radial view of an embodiment of the knob of the plunger that, in this embodiment, is generally cylindrical. The knob has projections 51 and recesses 52 that assist the user to rotate the knob of the plunger when implanting the drug depot.

FIG. 2B illustrates an expanded view of the plunger tip 60, which may be complementary to the proximal end 31 of the drug pellet 30 that allows the plunger tip 60 to snuggly fit within the proximal end of the drug pellet 30 for easier drug delivery. The distal end of the drug pellet 32 may be rounded for easier insertion at the desired site.

Drug Depot

In various embodiments, the device comprises a drug depot. A drug depot comprises a physical structure to facilitate implantation and retention in a desired site (e.g., a synovial joint, a disc space, a spinal canal, a tissue of the patient, etc.). The drug depot also comprises the drug. The term "drug" as used herein is generally meant to refer to any substance that alters the physiology of a the patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 cm to about 5 cm from the implant site.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, gels, coating, matrices, wafers, pills, cartridges, pellets or other pharmaceutical delivery compositions. A depot may comprise a biopolymer that is either biodegradable or non-degradable. A depot may comprise a biopolymer that may provide for immediate release or sustained release or controlled release. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, or combinations thereof.

In various embodiments, the drug depot comprises drug pellets loaded with a therapeutically effective amount of the therapeutic agent, wherein the pellets are injected into a synovial joint, a disc space, a spinal canal, or a soft tissue surrounding the spinal canal. In various embodiments, the drug pellets comprise a gel in viscous form and microspheres loaded with a therapeutic agent, wherein the combination of gel and microspheres are positioned into a synovial joint, disc space, a spinal canal, or a soft tissue surrounding the spinal canal of a subject.

A "therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In one exemplary embodiment, an expanded view of the drug depot in the form of a pellet is depicted in FIG. 3A. In this embodiment, the pellet 30 is bullet shaped, however, the pellet can be any shape, such as for example, spherical, substantially spherical, flaked, rod shaped, square, oval, etc. The proximal end 31 of the drug pellet 30 may allow the plunger tip to snuggly fit within the proximal end of the drug pellet 30 for easier drug delivery. The distal end of the drug pellet 32 may be rounded for easier insertion at the site.

In various embodiments, the drug pellet comprises a bullet-shaped body that is made from a biodegradable material. In alternative embodiments, the body may be made from a non-biodegradable material. A non-biodegradable body could be a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysacharides (Saber technology), polycapralactone, polyfumarate, tyrosine polycarbonate, etc. The body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

In various embodiments, the drug depot is in the form of a pellet. Pellets include, but are not limited to, substantially spherical, rod shaped, square, oval shaped particles having, in various embodiments, an aspect ratio (a ratio of the length of the pellet divided by the width found at an angle of 90° in respect to the length) which is less than about 4.0 to about 1.0.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

In various embodiments, the API is layered on the solid core of the pellet by solution or suspension layering or powder layering techniques. In solution or suspension layering, an API and any inactive ingredients (excipients, binders, etc.) are suspended or dissolved in water or an organic solvent. The resulting liquid is sprayed onto the outside of a core particle, which may include, for example, non-pareil sugar seed (sugar sphere), microcrystalline cellulose pellets and the like, to make the pellet having the desired potency. Solution or suspension layering may be conducted using a wide variety of process techniques, for example, by fluidized bed, Wurster bottom spray techniques, or the like. When the desired potency has been achieved, pellets are dried to the desired residual moisture content. Any oversized or undersized product may be removed by sieving, and the resulting pellets are narrow in size distribution.

Powder layering may also be used to make the drug pellets. Powdered layering involves the application of a dry powder to the pellet core material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In one embodiment, the pellet is made using a core of a core of biodegradable material, such as, for example, polyglactin, polylactone, polylactide, etc. The core is then coated with a thin layer of the API, such as an anti-inflammatory agent, analgesic agent, etc. by solution, suspension, or powdered layering until the desired potency is achieved.

In various embodiments, the drug pellets can be different sizes, for example, from a length of from about 0.5 mm to 5 mm and have a diameter of from about 0.01 to about 2 mm. The layer or layers will each have a layer thickness of from about 0.005 to 1.0 mm, such as, for example, from 0.05 to 0.75 mm.

Like the cannula, needle, or plunger, in various embodiments, the drug depot (e.g., pellet, cartridge, etc.) may have dose indicator markings (e.g., numbers, lines, letters, radiographic markers, etc.) to indicate the number of drug depots delivered. In various embodiments, radiopaque marks are positioned on the depot at opposite ends of the depot to assist in determining the position of the depot relative to the treatment site. For example, the radiopaque marker could be a spherical shape or a ring around the depot.

Drug Cartridge

In various embodiments, the drug depot is housed in a drug cartridge. The drug cartridge for delivering a drug pellet to a site beneath the skin of a patient. The drug cartridge comprises one or more drug pellets contained within a channel of the drug cartridge, the drug cartridge having a proximal end and a distal end, the proximal end of the drug cartridge having an opening to receive the one or more drug pellets and a plunger, the distal end of the cartridge having an opening for receiving the plunger and passage of the drug depot, wherein movement of the plunger to an extended position moves the one or more drug pellets within the channel of the cartridge out the distal end of the drug cartridge.

In various embodiments, the drug cartridge can be a capsule or matrix that holds one or more drug pellets. The drug cartridge may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or a combination thereof. In various embodiments, the drug cartridge is not biodegradable.

FIG. 3B illustrates a radial view of an embodiment of a drug cartridge 37 that has a proximal opening in the form of a channel 36 for loading the one or more drug pellets and for slidably receiving the plunger tip over the longitudinal axis of the drug cartridge. The one or more drug pellets are also slidably receivable over the longitudinal axis within the channel of the drug cartridge. In this way, when the plunger tip is moved it can push the drug pellet out of the drug cartridge to release it to the distal end of the cannula or needle and then to the target site.

FIG. 3C illustrates a side sectional view of an embodiment of a single dose drug cartridge 37 that has a proximal end 38 and distal end 39. The proximal end of the cartridge has an opening in the form of a channel 36 for loading the drug pellet 42 and for slidably receiving the plunger tip over the longitudinal axis of the drug cartridge. The one or more drug pellets are also slidably receivable over the longitudinal axis within the channel 36 of the drug cartridge. In this way, the plunger tip is capable of pushing the drug pellet 42 along channel 36 and guiding it out the distal end opening 33 out of the drug cartridge to release it to the distal end of the cannula or needle and then to the target site. In various embodiments, the drug cartridge will remain in the drug depot chamber, in other embodiments, the drug cartridge will remain within the distal end of the cannula or needle and only the one or more drug pellets will be dispensed.

FIG. 3D illustrates a side sectional view of an embodiment of multi-dose drug cartridge 37 (e.g., two, three, four, five, six, seven, eight, nine, ten, eleven doses, etc.) that has a proximal end 38 and distal end 39. The proximal end of the cartridge has an opening in the form of a channel 36 for loading the more than one drug pellet (shown are three 42, 44, and 46) and for slidably receiving the plunger tip over the longitudinal axis of the drug cartridge. The one or more drug pellets are also slidably receivable over the longitudinal axis within the channel 36 of the drug cartridge. In this way, the plunger tip is capable of pushing one or more drug pellets (42, 44, and 46) along channel 36 and guiding them out distal end opening 33 out of the drug cartridge 37 to release it to the distal end of the cannula or needle and then to the target site.

FIG. 3E illustrates a side sectional view of an embodiment of multi-dose drug cartridge 37 that has a proximal end 38 and distal end 39. The proximal end of the cartridge has an opening in the form of a channel 36 for loading the more than one drug pellet (shown are three 42, 44, and 46) and for slidably receiving the plunger tip 60 over the longitudinal axis of the drug cartridge. The one or more drug pellets are also slidably receivable over the longitudinal axis within the channel 36 of the drug cartridge. In this way, the plunger tip 60 is capable of pushing one or more drug pellets (42, 44, and 46) along channel 36 and guiding them out the distal end opening 33 out of the drug cartridge 37 to release them to the distal end of the cannula or needle and then to the target site. In the embodiment shown, drug pellet 46 is released. In various embodiments, the drug cartridge will remain in the drug depot chamber, in other embodiments, (not having a drug depot chamber) the drug cartridge will remain within the distal end of the cannula or needle and only the one or more drug pellets will be dispensed.

The drug device components (e.g., cannula or needle, plunger, handle, engagement means, etc.) may be disposable and sterilizable. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, the drug cartridge provides the advantages of ease of manufacturing in the terminal sterilization process. If the drug pellets are preloaded in the manufacturing process, gamma radiation may be required at higher does to sterilize the drug depot loaded in the cannula or needle. This is particularly so when the cannula or needle is made from steel or metal. Thus, to sterilize the loaded depot, the dose of gamma rays must be high enough to penetrate the metal, which may destroy the API in the drug depot. By providing a drug cartridge, for example, made of plastic, the drug cartridge and drug pellets in the cartridge can be sterilized, without destroying the API and then subsequently loaded by the manufacturer or the user (e.g., surgeon, physician, nurse, etc.). Further, loading the drug depot into the drug chamber or cannula is easier. This is particularly so when dealing with multi-dose drug pellets that are relatively small (e.g., 0.7 mm to 1 mm diameter for an 18 gauge needle or cannula), the user typically cannot grasp these small pellets and load them into the device. By providing them in a drug cartridge, the user does not have to substantially manipulate the individual drug pellets and the risk of contaminating the pellets particularly with sterilized pellets is reduced.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In various embodiments, a kit is provided which may include additional parts along with the drug depot device combined together to be used to implant the drug depot. The kit may include the drug depot device in a first compartment. The second compartment may include the drug cartridge, and any other instruments needed for the implant. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

FIG. 4 illustrates a side view of an embodiment of the drug depot device 10 which is assembled and loaded with a drug pellet 30. In this illustrated embodiment, the needle or cannula 24 has a proximal end in the direction of the opening 16, which receives the drug depot. The distal end of the cannula or needle is capable of insertion to the site beneath the skin of the patient and has an opening 26 for passage of the drug depot. In the illustrated embodiment shown in FIG. 4, the drug depot device does not have a drug depot chamber. Rather, the drug pellet 30 for delivery is loaded in opening 16. The drug depot device comprises a handle 12 disposed around the hub of the cannula, which has internal threading 18 for engaging the plunger. The handle may have contours 14 for easily grasping the device during insertion of the drug depot and the handle may extend 22 over a portion of the cannula or needle. The plunger 58 may have a knob 50 and engagement means 56 (shown as external threading) for engaging the internal threading 18 of the handle or hub. The plunger has a second end that includes a tip 60, which is capable of moving the drug depot within the cannula. Rotation of the knob 50 of the plunger 58 along the threading 18 of the hub or handle moves the tip of the plunger 60 to the extended position to deliver the drug depot from the distal end of the cannula to the site beneath the skin of the patient. The drug pellet 30 may have its proximal end 31 that allows the plunger tip to snuggly fit within the proximal end of the drug pellet 30 for easier drug delivery. The distal end of the drug pellet 32 may be rounded for easier insertion at the site. Markings 19 indicate the number of drug depots delivered, or location at or near the site beneath the skin may be provided. In the embodiment shown in FIG. 4, the plunger is in one of its retracted positions, so no drug pellet is dispensed.

FIG. 5 illustrates a side view of an embodiment of the drug depot device 10 which is assembled and loaded with a multi-dose drug cartridge 37. In this illustrated embodiment, the needle or cannula 24 has a proximal end in the direction of the opening 16, which receives the drug depot. The distal end of the cannula or needle is capable of insertion to the site beneath the skin of the patient and has an opening 26 for passage of the drug depot. In the illustrated embodiment shown in FIG. 5, the drug depot device does not have a drug depot chamber. Rather, the drug cartridge 37 for delivery is loaded in opening 16. The drug depot device comprises a handle 12 disposed around the hub of the cannula, which has internal threading 18 for engaging the plunger. The handle may have contours 14 for easily grasping the device during insertion of the drug depot and the handle may extend 22 over a portion of the cannula or needle. The plunger 58 may have a knob 50 and engagement means 56 (shown as external threading) for engaging the internal threading 18 of the handle or hub. The plunger has a second end that includes a tip 60, which is capable of moving the drug depot within the cannula.

Rotation of the knob 50 of the plunger 58 along the threading 18 of the hub or handle moves the tip of the plunger 60 to the extended position to deliver the drug depot from the distal end of the cannula to the site beneath the skin of the patient. In FIG. 5 the multi-dose drug cartridge 37 has an opening in the form of a channel 36 for loading the more than one drug pellet (shown are three 42, 44, and 46) and for slidably receiving the plunger tip 60 over the longitudinal axis of the drug cartridge. The one or more drug pellets are also slidably receivable over the longitudinal axis within the channel 36 of the drug cartridge. In this way, the plunger tip 60 is capable of pushing one or more drug pellets (42, 44, and 46) along channel 36 and guiding them out distal end 39 from opening 33 out of the drug cartridge 37 to release them to the distal end of the cannula or needle 26 and then to the target site. In the embodiment shown, drug pellet 46 is released in the target site, while the drug cartridge stays inside of the cannula or needle. Markings 19 indicate the number of drug depots delivered, or location at or near the site beneath the skin may be provided. In the embodiment shown in FIG. 5, the plunger is in one of its extended positions to release the pellet.

Figure 6:
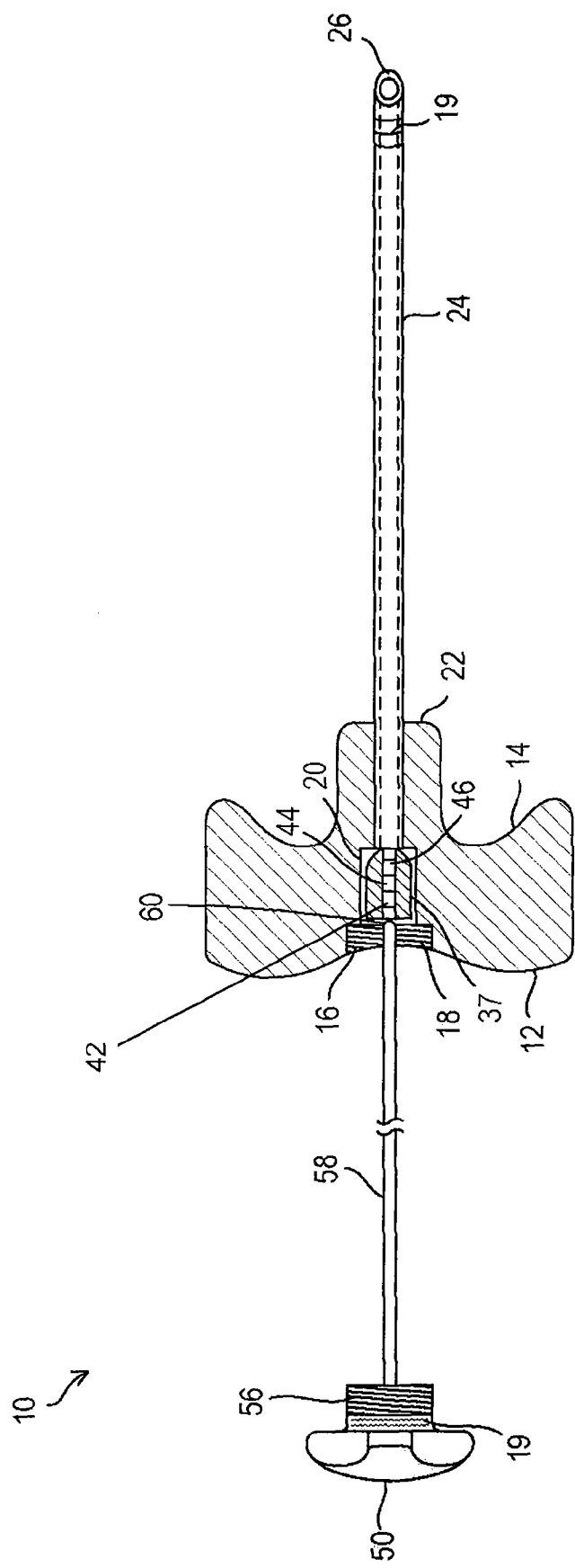
FIG. 6 illustrates a side view of an embodiment of the drug depot device loaded with a drug cartridge inside the drug depot chamber. The plunger is in one of the retracted positions.

FIG. 6 illustrates a side view of an embodiment of the drug depot device 10 which is assembled and loaded with a multi-dose drug cartridge 37. In this illustrated embodiment, the needle or cannula 24 has a proximal end in the direction of the opening 16, which receives the drug depot. The distal end of the cannula or needle is capable of insertion to the site beneath the skin of the patient and has an opening 26 for passage of the drug depot. In the illustrated embodiment shown in FIG. 6, the drug depot device has a drug depot chamber 20 loaded with a drug cartridge 37 for delivery. The drug cartridge is loaded in opening 16. The drug depot device comprises a handle 12 disposed around the drug depot chamber. The drug depot chamber 20 or the handle 12 includes internal threading 18 for engaging the plunger. The handle may have contours 14 for easily grasping the device during insertion of the drug depot and the handle may extend 22 over a portion of the cannula or needle. The plunger 58 may have a knob 50 and engagement means 56 (shown as external threading) for engaging the internal threading 18 of the handle or drug depot chamber 20. The plunger has a second end that includes a tip 60, which is capable of moving the drug depot within the cannula. Rotation of the knob 50 of the plunger 58 along the threading 18 moves the tip of the plunger 60 to the extended position to deliver the drug depot from the distal end of the cannula to the site beneath the skin of the patient.

In FIG. 6 the multi-dose drug cartridge 37 has an opening in the form of a channel for loading the more than one drug pellet (shown are three 42, 44, and 46) and for slidably receiving the plunger tip 60 over the longitudinal axis of the drug cartridge. The one or more drug pellets are also slidably receivable over the longitudinal axis within the channel of the drug cartridge. In this way, the plunger tip 60 is capable of pushing one or more drug pellets (42, 44, and 46) along the channel and guiding them out distal end opening of the channel out of the drug cartridge 37 to release them to the distal end of the cannula or needle 26 and then to the target site. In the embodiment shown, the drug cartridge is retained in the drug depot chamber. Markings 19 indicate the number of drug depots delivered, or location at or near the site beneath the skin may be provided. In the embodiment shown in FIG. 6, the plunger is in one of its retracted positions so no drug pellet is dispensed (shown by the half turn symbol).

In various embodiments, a method is provided for delivering a drug depot to a site beneath the skin of a patient, the method comprising: providing a device for delivering a drug depot, the device comprising a cannula having a proximal end and a distal end, the proximal end of the cannula having an opening to receive the drug depot, the distal end of the cannula capable of insertion to the site beneath the skin of the patient and having an opening for passage of the drug depot; and a plunger being slidably receivable within the opening of the proximal end of the cannula, the plunger having a first end and a tip at a second end, the first end being capable of moving the tip of the plunger to an extended position; inserting the distal end of the cannula and/or the plunger to the site beneath the skin of the patient; loading the drug depot for delivery in the cannula; positioning the plunger within the cannula and moving the plunger in the extended position thereby delivering the drug depot from the distal end of the cannula to the site beneath the skin of the patient.

In various embodiments, to administer the drug depot to the desired site, first the cannula or needle and/or plunger can be inserted through the skin and soft tissue down to the site of injection. In this embodiment, the plunger can be removed from the cannula or needle and the drug cartridge containing one or more drug pellets inserted into the cartridge chamber, the plunger now can push the one or more drug pellets out from the drug cartridge and out the distal end of the cannula to the desired site. The cannula or needle and/or plunger is then removed from the site. In this way, the device allows the user to precisely control implant location, accurate spacing, and drug distribution.

Figure 7:
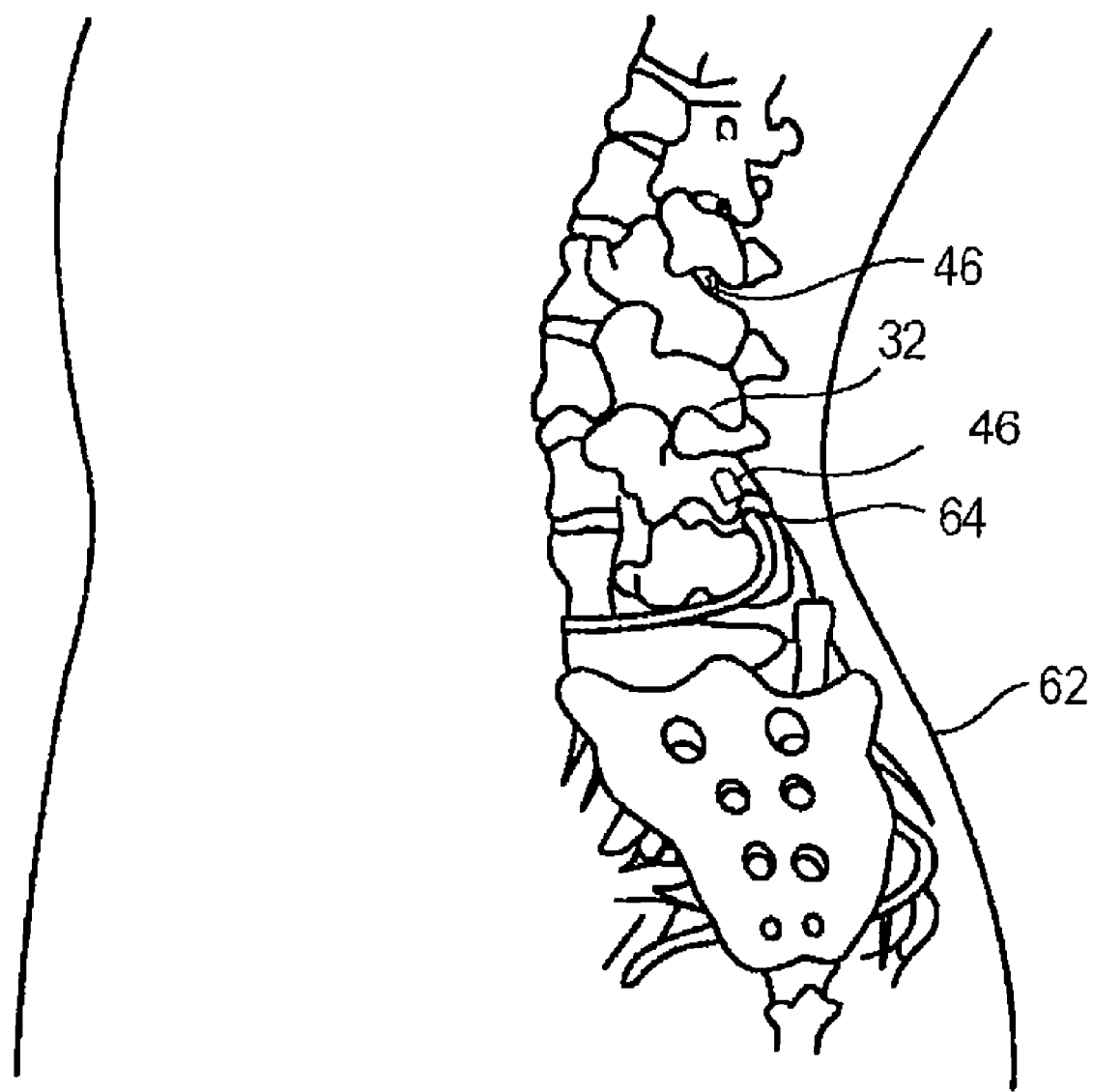
FIG. 7 illustrates a schematic dorsal view of the spine and sites where one or more drug depots may be inserted.

FIG. 7 illustrates a schematic dorsal view of the spine and sites where one or more drug depots may be inserted using the drug depot device. The cannula or needle or plunger is inserted beneath the skin 62 to a spinal site 64 (e.g., spinal disc space, spinal canal, soft tissue surrounding the spine, etc.) and one or more drug depots 46, 32 are delivered to various sites along the spine. Although the spinal site is shown, the device can be used to deliver a drug depot to any site beneath the skin, including, but not limited to, at least one muscle, ligament, tendon, cartilage, synovial joint, spinal disc, spinal foraminal space, near the spinal nerve root, facet joint, or spinal canal.

In various embodiments, the seal between the plunger tip and the cannula or needle can be air tight so that when the cannula or plunger penetrates the skin, at times, fluid (e.g., blood, spinal fluid, synovial fluid, etc.) may be drawn up into the cannula or needle. This fluid will be expelled when the plunger is re-inserted into the cannula or needle and the drug depot is released. In other embodiments, the seal between the plunger tip and the cannula or needle is not required to be airtight. In other embodiments, the seal between the plunger tip and the cannula or needle is airtight.

The device may be used for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

In various embodiments, the drug depot device is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots in a quantity of pharmaceutical composition that can be deposited at the target site as needed for treatment of pain, inflammation or other disease or condition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for delivering a drug depot to a site at or near a spinal column of a patient, the device comprising:
   a cannula having a diameter, and a proximal end and a distal end, the proximal end of the cannula having an opening and a drug depot chamber to receive the drug depot, the distal end of the cannula for insertion at or near the spinal column and having an opening for passage of the drug depot, and the drug depot having a proximal end configured for attaching to a plunger and a distal end configured to facilitate insertion into the site, is disposed within the drug depot chamber of the cannula, the drug depot chamber being immovably disposed to the cannula at the proximal end and has a diameter larger than the diameter of the cannula;
   a plunger being slidably receivable within the opening of the proximal end of the cannula and the drug depot chamber, the plunger having a first end and a tip at a second end that is configured to fit within said proximal end of said drug depot, the first end moves the tip of the plunger to an extended position; wherein the openings of the proximal and distal ends permit passage of the drug depot and wherein the movement of the tip of the plunger to the extended position causes the tip of the plunger to push the drug depot out of the drug depot chamber and out of the distal end of the cannula and cause delivery of the drug depot from the distal end of the cannula to the site at or near the spinal column of the patient; and
   a drug cartridge having a proximal end and distal end, the proximal end of the cartridge having an opening in the form of a channel for loading at least one drug depot and for slidably receiving the plunger tip over a longitudinal axis of the drug cartridge, wherein the drug pellets are slidably receivable over the longitudinal axis within the channel of the drug cartridge such that the plunger tip is configured for pushing one or more drug pellets along the channel and guiding the drug pellets out the distal end opening to release the drug pellets to the distal end of the cannula, wherein the drug cartridge will remain in the drug depot chamber.

2. A device for delivering a drug depot according to claim 1, wherein the cannula comprises a hub surrounding the opening of the proximal end of the cannula and the plunger engages the hub to move the tip of the plunger to the extended position to push the drug depot out of the drug depot chamber to deliver the drug depot out of the distal end of the cannula and to the site at or near the spinal column.

3. A device for delivering a drug depot according to claim 1, wherein the drug depot chamber has more than one drug depot disposed therein.

4. A device for delivering a drug depot according to claim 2, wherein the threading of the hub comprises internal threading and the threading of the first end comprises external threading that pair when: (i) the first end is rotated in a clockwise direction causing the tip of the plunger to move in the extended position causing the tip of the plunger to push the drug depot out of the drug depot chamber and out of the distal end of the cannula or (ii) the first end is rotated in a counterclockwise direction to secure the tip of the plunger in a retracted position in a direction toward the hub and away from the drug depot.

5. A device for delivering a drug depot according to claim 1, wherein the drug depot is at least a sterilizable drug depot and/or a biodegradable drug depot.

6. A device for delivering a drug depot according to claim 1, wherein the site is at least one muscle, ligament, tendon, cartilage, spinal disc, spinal foraminal space, near the spinal nerve root, facet joint, or spinal canal.

7. A device for delivering a drug depot according to claim 2, wherein at least one of: (i) a handle is fixed to at least the hub of the cannula, (ii) a handle is fixed to at least the hub of the cannula, and the handle, first end, plunger or hub includes dose indicator markings to indicate the number of drug depots delivered, or (iii) the plunger, cannula or drug depot include markings that indicate location at or near the site beneath the skin.

8. A device for delivering a drug depot to a site beneath the skin of a patient, the device comprising:
   a needle having a diameter, and a proximal end and a distal end, the proximal end of the needle having an opening to receive the drug depot and a generally cylindrical hub surrounding the opening of the proximal end of the needle, the distal end of the needle having a tip capable of passage through the skin of the patient and an opening for passage of the drug depot; wherein the drug depot has a proximal end configured for attaching to a plunger and a distal end configured to facilitate insertion into the site,
   a plunger being slidably receivable within the opening of the proximal end of the needle and movable to an extended position, the plunger having a knob at a first end and a tip at a second end that is configured to fit within said proximal end of said drug depot, the knob having threading for engaging the hub of the needle and the hub of the needle comprising threading for engaging the knob of the plunger, wherein rotation of the knob of the plunger along the threading of the hub moves the tip of the plunger to the extended position causing the tip of the plunger to push the drug depot from the distal end of the needle to effect delivery of the drug depot to the site beneath the skin of the patient, wherein the proximal end of the needle further comprises a drug depot chamber contacting the opening of the needle and the threading of the hub, and the drug depot chamber has a diameter larger than the diameter of the needle; and a drug cartridge having a proximal end and distal end, the proximal end of the cartridge having an opening in the form of a channel for loading at least one drug depot and for slidably receiving the plunger tip over a longitudinal axis of the drug cartridge, wherein the drug pellets are slidably receivable over the longitudinal axis within the channel of the drug cartridge such that the plunger tip is configured for pushing one or more drug pellets along the channel and guiding the drug pellets out the distal end opening to release the drug pellets to the distal end of the cannula, wherein the drug cartridge will remain in the drug depot chamber.

9. A device for delivering a drug depot according to claim 8, wherein the drug depot chamber receives one or more drug depots and the tip of the plunger.

10. A device for delivering a drug depot according to claim 8, wherein the drug depot is at least a sterilizable drug depot or a biodegradable drug depot.

11. A device for delivering a drug depot according to claim 8, wherein the threading of the hub comprises internal threading and the threading of the knob comprises external threading that pair when: (i) the knob is rotated in a clockwise direction causing the tip of the plunger to move in the extended position causing the tip of the plunger to push the drug depot out of the distal end of the needle or (ii) the knob is rotated in a counterclockwise direction to secure the tip of the plunger in a retracted position in a direction away from the drug depot.

12. A device for delivering a drug depot according to claim 8, wherein at least one of: (i) a handle is fixed to at least the hub of the needle; (ii) the knob, plunger or hub includes dose indicator markings to indicate the number of drug depots delivered or (iii) the plunger, needle or drug depot include markings that indicate depth beneath the skin.

13. A device for delivering a drug depot to a site at or near a spinal column of a patient, the device comprising:

a cannula having a diameter and a proximal end and a distal end, the distal end of the cannula having an opening for passage of the drug depot, the proximal end of the cannula attached to a depot chamber, the drug depot chamber being immovably disposed to the cannula and having an opening to receive the drug depot, wherein the drug depot chamber has a diameter larger than the diameter of the cannula and contains the drug depot; wherein the drug depot has a proximal end configured for attaching to a plunger and a distal end configured to facilitate insertion into the site;

a plunger being slidably receivable within the opening of the drug depot chamber and within the cannula, the plunger having a first end and a tip at a second end that is configured to fit within said proximal end of said drug depot, the first end for moving the tip of the plunger to an extended position, wherein the openings of the drug depot chamber and distal end of the cannula permit passage of the drug depot and wherein the movement of the tip of the plunger to the extended position causes the tip of the plunger to push the drug depot out the drug depot chamber and out the distal end of the cannula to cause delivery of the drug depot to the site at or near the spinal column of the patient; and a drug cartridge having a proximal end and distal end, the proximal end of the cartridge having an opening in the form of a channel for loading at least one drug depot and for slidably receiving the plunger tip over a longitudinal axis of the drug cartridge, wherein the drug pellets are slidably receivable over the longitudinal axis within the channel of the drug cartridge such that the plunger tip is configured for pushing one or more drug pellets along the channel and guiding the drug pellets out the distal end opening to release the drug pellets to the distal end of the cannula, wherein the drug cartridge will remain in the drug depot chamber.

14. A device for delivering a drug depot according to claim 13, wherein the plunger is capable of insertion to the site at or near the spinal column.

15. A device for delivering a drug depot according to claim 13, wherein the device further comprises a handle attached to the drug depot chamber, the handle having threading aligned with the opening of the chamber and for engaging the first end of the plunger, and the first end of the plunger comprising threading for engaging the threading of the handle, wherein rotation of the first end of the plunger along the threading of the handle moves the tip of the plunger to the extended position causing the tip of the plunger to push the one or more drug pellets from the drug cartridge to the distal end of the cannula to deliver the one or more drug pellets to the site at or near the spinal column.

16. A method for delivering a drug depot to a site beneath the skin of a patient, the method comprising:

providing a device for delivering a drug depot, the device comprising a cannula having a diameter and a proximal end and a distal end, the proximal end of the cannula having an opening to receive the drug depot, the drug depot having a proximal end configured for attached to a plunger and a distal end configured to facilitate insertion into the site, the distal end of the cannula capable of insertion to the site beneath the skin of the patient and having an opening for passage of the drug depot; a plunger being slidably receivable within the opening of the proximal end of the cannula, the plunger having a first end and a tip at a second end that is configured to fit within said proximal end of said drug depot, the first end being capable of moving the tip of the plunger to an extended position; and a drug cartridge having a proximal end and distal end, the proximal end of the cartridge having an opening in the form of a channel for loading at least one drug depot and for slidably receiving the plunger tip over a longitudinal axis of the drug cartridge, wherein the drug pellets are slidably receivable over the longitudinal axis within the channel of the drug cartridge such that the plunger tip is configured for pushing one or more drug pellets along the channel and guiding the drug pellets out the distal end opening to release the drug pellets to the distal end of the cannula, wherein the drug cartridge will remain in the drug depot chamber;

inserting the distal end of the cannula and/or the plunger to the site beneath the skin of the patient;

loading the drug depot for delivery in a drug depot chamber that is attached to the cannula and has a diameter larger than the diameter of the cannula; and positioning the plunger within the cannula and moving the plunger in the extended position to cause only the tip of the plunger to push the drug depot from the distal end of the cannula to deliver the drug depot to the site beneath the skin of the patient.

17. A method for delivering a drug depot, according to claim 16, wherein (i) the site is at least one muscle, ligament, tendon, cartilage, synovial joint, spinal disc, spinal foraminal space, near the spinal nerve root, facet joint or spinal canal or (ii) the drug depot comprises at least one anti-inflammatory agent, analgesic agent, anabolic or anti-catabolic growth factor.

18. A device for delivering a drug depot according to claim 1, wherein the plunger is longer than the cannula and the tip of the plunger extends beyond the distal end of the cannula when the plunger is moved in the extended position.

19. A device for delivering a drug depot according to claim 8, wherein the plunger is longer than the needle and the tip of the plunger extends beyond the distal end of the needle when the plunger is moved in the extended position.

* * * * *

UNITED STATES PATENT AND TRADEMARK OFFICE
CERTIFICATE OF CORRECTION

| | | |
|---|---|---|
| PATENT NO. | : 8,221,358 B2 | Page 1 of 1 |
| APPLICATION NO. | : 11/942820 | |
| DATED | : July 17, 2012 | |
| INVENTOR(S) | : McKay | |

It is certified that error appears in the above-identified patent and that said Letters Patent is hereby corrected as shown below:

In Column 1, Line 65, delete "supraspinus" and insert -- supraspinous --, therefor.

In Column 1, Line 66, delete "intraspinus" and insert -- interspinous --, therefor.

In Column 9, Line 55, delete "papavereturn," and insert -- papaveretum, --, therefor.

In Column 10, Line 52, delete "polysacharides" and insert -- polysaccharides --, therefor.

In Column 10, Line 52, delete "polycapralactone," and insert -- polycaprolactone, --, therefor.

In Column 18, Line 65, in Claim 8, delete "site," and insert -- site; --, therefor.

In Column 19, Line 19, in Claim 8, delete "slidablv" and insert -- slidably --, therefor.

Signed and Sealed this
Thirtieth Day of October, 2012

David J. Kappos
*Director of the United States Patent and Trademark Office*